US005522396A

United States Patent [19]
Langer et al.

[11] Patent Number: 5,522,396
[45] Date of Patent: Jun. 4, 1996

[54] METHOD AND SYSTEM FOR MONITORING THE HEART OF A PATIENT

[75] Inventors: Alois A. Langer, Pittsburgh; Khalil J. Maalouf, Turtle Creek, both of Pa.

[73] Assignee: Cardiac Telecom Corporation, Turtle Creek, Pa.

[21] Appl. No.: 101,199

[22] Filed: Jul. 29, 1993

Related U.S. Application Data

[63] Continuation-in-part of Ser. No. 881,604, May 12, 1992.
[51] Int. Cl.$^6$ ................................................. A61B 5/0402
[52] U.S. Cl. .......................... 128/696; 128/904; 128/903
[58] Field of Search ..................................... 128/903, 904, 128/702, 706, 695, 696, 630; 364/413.06, 413.01, 413.04

[56] References Cited

U.S. PATENT DOCUMENTS

| | | | |
|---|---|---|---|
| 4,173,971 | 11/1979 | Karz | 128/904 |
| 4,531,527 | 7/1985 | Reinhold, Jr. et al. | 128/696 |
| 4,952,928 | 8/1990 | Carroll et al. | 128/903 |
| 5,038,800 | 8/1991 | Oba | 128/904 |

Primary Examiner—William E. Kamm
Attorney, Agent, or Firm—Ansel M. Schwartz

[57] ABSTRACT

The present invention pertains to a system for monitoring the health condition of a patient, such as the condition of the patient's heart. The system comprises a patient station having means for monitoring a predetermined bodily function of the patient and a patient transmitter for transmitting information relating to the bodily function. The system is also comprised of a secondary system remote from the patient at the patient station having means for activating the patient station such that information relating to the monitored bodily function can be transmitted from the patient station to the secondary station. The secondary station is in communication with the patient station. The present invention also pertains to a method of monitoring the health condition of a patient. The method comprises the steps of providing the patient with a device for monitoring a predetermined bodily function of the patient at a patient station. Then there is the step of activating the patient station from the secondary station remote from the patient at the patient station such that information relating to the predetermined bodily function of the patient can be transmitted to the secondary station.

15 Claims, 4 Drawing Sheets

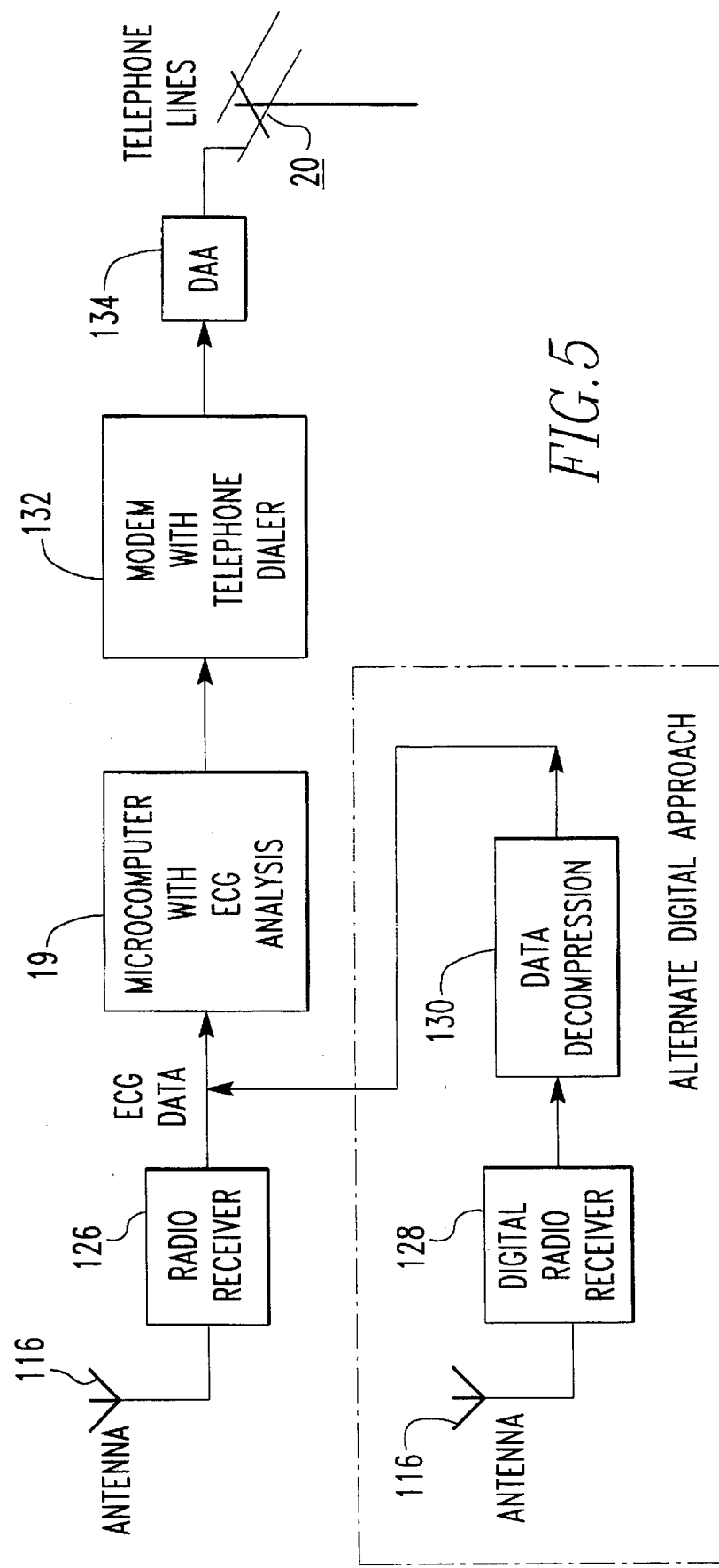

METHOD AND SYSTEM FOR MONITORING THE HEART OF A PATIENT

This is a continuation-in-part of copending application(s) Ser. No. 07/881,604 filed on May 12, 1992.

FIELD OF THE INVENTION

The present invention is related in general to heart monitors. More specifically, the present invention is related to a method and system which monitors a patient's heart remotely.

BACKGROUND OF THE INVENTION

Heart malfunction is one of the primary causes of death in humans. In order to detect and predict heart malfunctions, it is known to connect patients to a heart monitor. Typical heart monitors generate and display an electrocardiogram of the heartbeat and are directly connected to the patient with electrodes. Unfortunately, these heart monitors require the patient to reside in the hospital in dedicated telemetric beds. Further, the multitude of state of the art heart monitors necessary to monitor the often numerous heart patients represent undue complexity and expense. U.S. Pat. No. 4,173,971 by Karz, incorporated by reference, discloses a system for sending an electrocardiogram to a remote location, but does not provide for further support to assist in the response to a patient in need.

SUMMARY OF THE INVENTION

The present invention pertains to a system for monitoring the health condition of a patient. The system comprises a patient station having means for monitoring a predetermined bodily function of the patient and a patient transmitter for transmitting information relating to the bodily function. The system is also comprised of a secondary system remote from the patient station having means for activating the patient station such that information relating to the monitored bodily function can be transmitted from the patient station to the secondary station.

The present invention also pertains to a method of monitoring the health condition of a patient. The method comprises the steps of providing the patient with a device for monitoring a predetermined bodily function of the patient, such as the heart, at a patient station. Then there is the step of activating the patient station from the secondary station remote from the patient station such that information relating to the predetermined bodily function of the patient can be transmitted to the secondary station.

BRIEF DESCRIPTION OF THE DRAWINGS

In the accompanying drawings, the preferred embodiment of the invention and preferred methods of practicing the invention are illustrated in which:

FIG. 5 is a schematic representation of an analog and alternate digital embodiment of a tele-link.

DESCRIPTION OF THE PREFERRED EMBODIMENT

Figure 1:
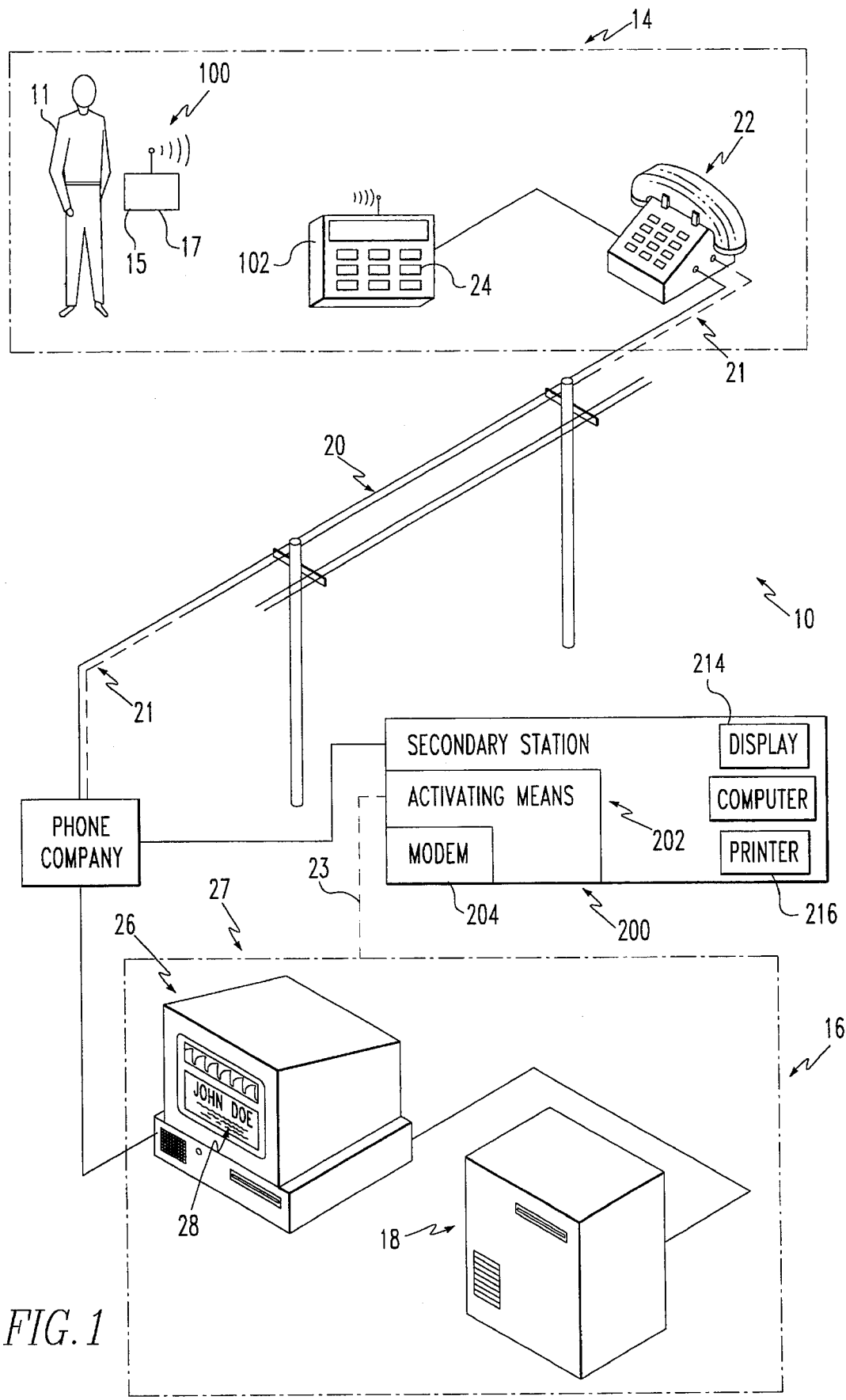
FIG. 1 is a schematic representation showing the system for monitoring the heart of a patient.

Referring now to the drawings wherein like reference numerals refer to similar or identical parts throughout the several views, and more specifically to FIG. 1 thereof, there is shown a system 10 for monitoring the health condition of a patient. The system comprises a patient station 14 having means for monitoring a predetermined bodily function of the patient, means 17 for detecting predetermined events relating to the monitored bodily function in the patient and a patient transmitter 100 for transmitting information relating to the monitored bodily functions. The system 10 also comprises a central station 16 in communication with the patient transmitter 100 for receiving the transmitted information. There is also a database 18 in communication with the central station 16 for storing and providing patient data to the central station 16 when a predetermined event occurs and display means 27, in communication with the central station 16 and the database 18, for displaying the patient data and the transmitted information.

In a preferred embodiment, the system 10 monitors the heart of the patient 11. In this embodiment, the system 10 is comprised of a patient station 14 having means 15 for generating an electrocardiogram of the patient. There is also means 17 for detecting predetermined cardiological events in the patient. The detecting means 17 is in communication with the generating means 15. Additionally, there is a patient transmitter 100 for transmitting the electrocardiogram. The transmitter 100 is in communication with the generating means 15. The system 10 additionally is comprised of a central station 16 in communication with the patient transmitter 100 for receiving a transmitted electrocardiogram. There is also a database 18 in communication with the central station 16 for storing patient data and providing patient data to the central station 16. Additionally, there is display means 27 in communication with the central station 16 and the database 18 for displaying the patient data and the transmitted electrocardiogram. It should be noted that the system 10 can be used to monitor any one or more of a multitude of bodily functions, such as the brain, lungs and/or blood of the patient, to name but a few of the possible monitored bodily functions.

Figure 2:
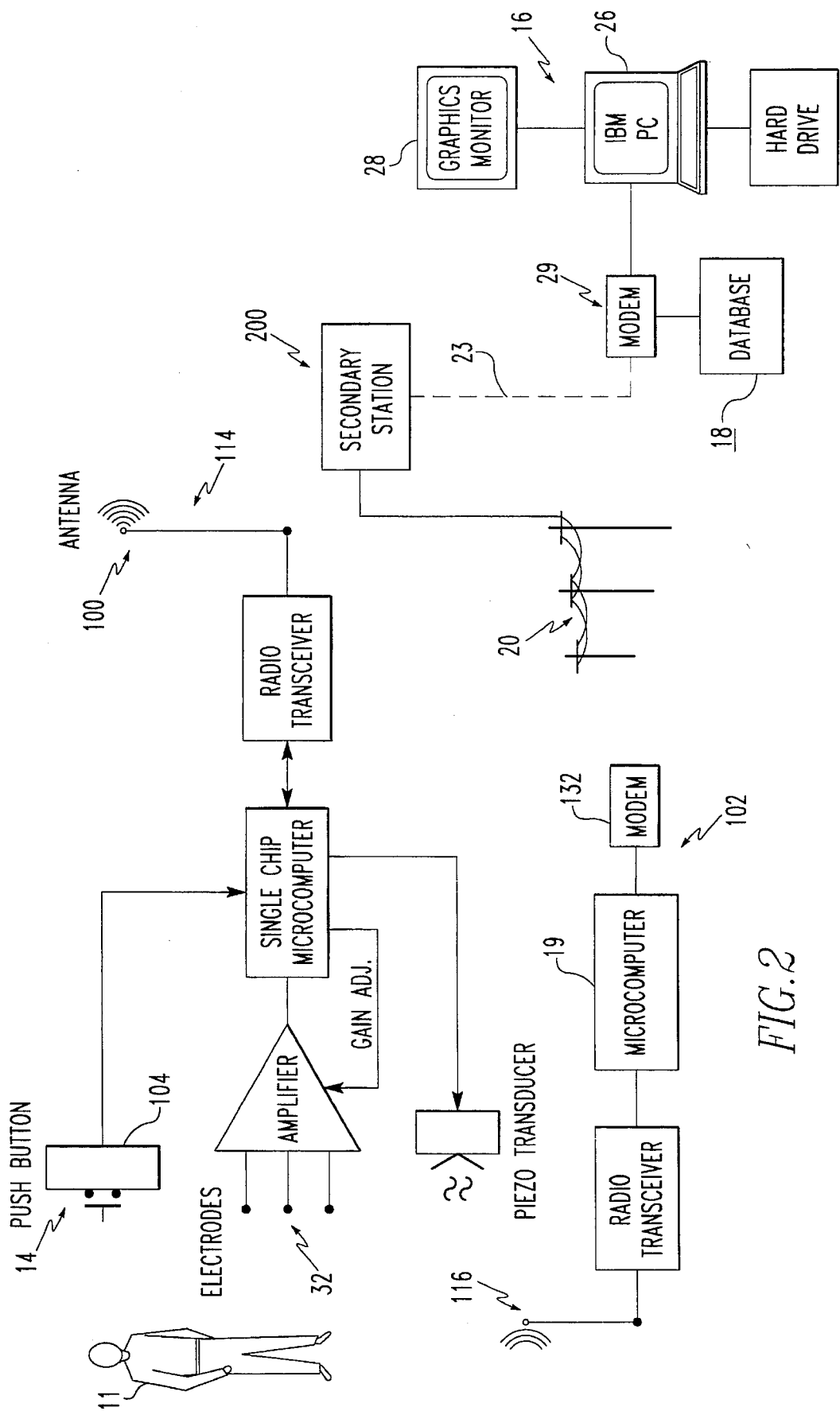
FIG. 2 is a schematic representation of a system for monitoring the heart of a patient.

In a preferred embodiment, and as shown in FIG. 2, the patient station 14 includes a small electronic unit called a patient transmitter 100 that is carried by the patient. The patient station 14 communicates with the central station 16 over a telecommunications line 20, preferably through the patient's own telephone via a tele-link 102 of the patient station 14. The central station 16 has a central receiver or modem 29 for receiving the electrocardiogram from the telecommunications line 20. The patient station 14 has a keypad 24, as shown in FIG. 1, for inputting information such as the hospital phone number and patient identification numbers into it.

It is also desirable for the central station 16 to communicate with the patient through the system 10. Accordingly, the central station 16 can include a central transmitter for transmitting information from the central station 16 to the patient station 14 over the telecommunications line 20. The patient station 14 includes a patient receiver, such as a modem 132, for receiving information from the central station 16 over the telecommunications lines 20. Preferably, the central station 16 is located within the patient's hospital and includes a computer 26 and display screen 28. The central transmitter and receiver can also be a modem 29 as mentioned above.

The present invention is a system 10 for monitoring the health condition of a patient 11 which comprises a patient station 14 having means for monitoring a predetermined bodily function of the patient 11, and a patient transmitter 100 which is preferably part of a tele-link unit 102. The system 10 also comprises a secondary station 200 which is remote from the patient station 14. The secondary station 200 has means 202 for activating the patient station such that information relating to the monitored bodily function can be transmitted from the patient station to the secondary station. The secondary station 200 can be used, for instance, by the patient's physician to interface with the remote state 14 so that the physician can review the health condition of his patient as desired.

Preferably, the activating means comprises means for creating a communication channel between the patient station 14 and the secondary station 200, such as a modem 204. In a preferred embodiment, the monitoring means includes means 15 for generating an electrocardiogram of the patient 11.

Figure 6:
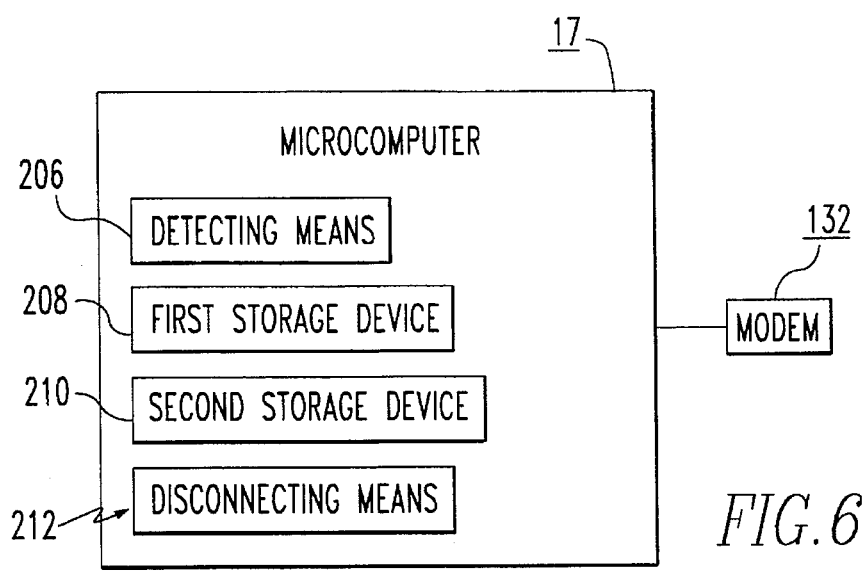
FIG. 6 is a block diagram of the microcomputer of the patient station.

Preferably, as shown in FIG. 2, the patient station 14 has a microcomputer 19. As shown in FIG. 6, the microcomputer 19 can have means for storing electrocardiogram information. Preferably, the microcomputer 19 also comprises means 206 for detecting predetermined cardiological events. Preferably, the storing means includes a first storage device 208 for storing predetermined cardiological events. The storage means can also include a second storage device 210 for storing the electrocardiogram generated by the generating means for a predetermined period of time.

Preferably, the secondary station 200 is part of a system 10 which also has the previously described central station 16 database 18 and display means 28. In this manner, the patient station 14 can transmit electrocardiogram information of the patient 11 to both the central station 16 and the secondary station 200. The secondary station 200 can be in the possession of a doctor of the patient 11 and can be used to interface with the patient station 14 at the physician's discretion. For instance, the physician, by using the secondary station 200, could retrieve the most recent cardiogram information from the second storage device 210 of the patient station microcomputer 19. Also, the first storage device 208 can be accessed to review any detected cardiological events such as arrythmia, tachycardia, etc.

As shown in FIG. 1, the connection of the secondary station 200 with the patient station 14 can be accomplished in a variety of ways. In a first embodiment, the patient station 14 has a single telecommunication line 20 through which both the central station 16 and the secondary station 200 communicate with the patient station 14. In this embodiment, the patient station 14 has means 212 for disconnecting the secondary station 200 from the patient station 14 when a predetermined cardiological event occurs. In this manner, the patient station 14 can transmit electrocardiogram information to the central station 16, such as the hospital, over the first telecommunication line 20. Preferably, as shown in FIG. 6, the disconnecting means 212 is integrated into the microcomputer 19.

In another embodiment, the patient station 14 has two independent telecommunication lines 20 and 21. Telecommunication line 21 is shown as a dotted line in FIG. 1. The central station 16 is in communication with the first telecommunication line 20 while the secondary station 200 is in communication with the second telecommunication line 21. In this embodiment, the secondary station 200 does not have to be cut off if a predetermined cardiological event happens to occur.

In a third embodiment, the secondary station 200 can communicate through the central station 16, such as through telecommunication line 23, shown as a dashed line in FIG. 1. In this embodiment, in order to contact the patient station 14, the secondary station must first contact the central station 16 which in turn contacts the patient station 14. In this manner, the patient station 14 can have one telecommunication line 20 and the secondary station 200 does not have to be cut off if a predetermined cardiological event occurs.

The invention is also a method of monitoring the health condition of a patient 11. The method includes the first step of monitoring a predetermined bodily function of a patient. Then, there is the step of automatically detecting predetermined events relating to the monitored bodily function. Next, there is the step of transmitting information relating the monitored bodily function to a central station 16 along with identification of the patient if a predetermined event relating to the monitored bodily function occurs. Then, there is the step of retrieving data about the patient from a database 18. Next, there is the step of transmitting the patient's data from the database 18 to the central station 16.

In a preferred embodiment, the method is used to monitor the heart condition of a patient 11. In this embodiment, the method includes the first step of taking an electrocardiogram of a patient. Then, there is the step of automatically detecting predetermined cardiological events in the electrocardiogram. Next, there is the step of transmitting the electrocardiogram to a central station 16 along with identification of the patient if a predetermined cardiological event occurred. Then, there is the step of retrieving data about the patient from a database 18. Next, there is the step of transmitting the patient's data from the database 18 to the central station 16.

Preferably, the detecting step includes the step of automatically diagnosing the electrocardiogram. Preferably, after the retrieving step, there is the step of contacting the patient 11 and after the diagnosing step, there is the step of sounding an alarm. Preferably, after the transmitting step, there is the step of displaying the electrocardiogram and the corresponding patient data on a display screen 28. Preferably, the transmitting step includes the step of transmitting the electrocardiogram over a telecommunication line 20 and before the taking step, there is the step of programming the patient station 14 with patient identification and the phone number of the central station 16.

The present invention is also a method of monitoring the health condition of a patient 11. The method comprises the steps of providing the patient 11 with a device for monitoring a predetermined bodily function. The method further comprises the step of activating the patient station 14 from a secondary station 200 remote from the patient station 14 such that information relating to the predetermined bodily function of the patient 11 can be transmitted to the secondary station 200.

Preferably, the providing step includes the step of providing the patient with a device 15 for generating an electrocardiogram of the patient. Preferably, after the providing step, there is the step of taking an electrocardiogram of the patient at the patient station 14. Preferably, after the taking step, there is the step of storing information relating to the electrocardiogram and the activating step includes the step of retrieving stored electrocardiogram information.

Preferably, after the taking step, there are the steps of automatically detecting predetermined cardiological events in the electrocardiogram, automatically transmitting the electrocardiogram to a central station 16 remote from the patient station 14 along with identification of the patient 11 if a predetermined cardiological event has occurred, automatically retrieving data about the patient 11 having a predetermined cardiological event from a database 18 in communication with the central station 16 and automatically transmitting the data to the central station 16 from the database 18.

In the operation of the preferred embodiment, a patient 11 who is in medical need of heart monitoring is assigned a patient station 14 from his doctor at the hospital. The patient station 14 is comprised of a patient transmitter 100 which is worn by the patient, and a tele-link 102 which is operationally connected to a telephone where the patient is located. The doctor then programs the patient station 14 with the patient's identification number and the phone number of the hospital's central station 16. A keypad 24 is provided on the patient station 14 for inputting the information. A display window 34 is provided for displaying the information. Once the patient station 14 is operational, it is set in a dormant state and the patient is allowed to go home. Alternatively, the patient can go to a hotel, a friend's home, other type of health care facility or even another room or bed in the hospital which does not have dedicated instrumentation to provide heart monitoring of the patient 11, to name but a few of the many patient stations to which the patient can go, as long as there is at least a phone nearby.

During its dormancy, the patient station 14 periodically activates to check if it is connected to the telecommunication line 20. Once home, the patient links the patient station 14 to the telephone line 20 and dials the phone number of the hospital's central station 16 to establish the connection with the central station 16. Electrodes 32 from the patient transmitter 100 of the patient station 14 are connected to the patient for monitoring his heart 12. The electrocardiogram signal generated by the patient transmitter 100 of the patient station 14 is analyzed by the first computer 17 having a computer program within the tele-link 102 to detect predetermined threshold events, such as arrythmia or tachycardia. The patient transmitter 102 can be a fully analog system as disclosed in patent U.S. Pat. No. 3,195,535 (incorporated by reference), which shows a complete miniature radiating electrocardiograph, or preferably, it can be digital transmitter which codes the electrocardiogram data into digital representation. In this preferred embodiment, the electrocardiogram amplifier 120 is similar to that in U.S. Pat. No. 3,724,455 by Ungar, incorporated by reference, at block 70, while the A-D and digital data compressor 122 is disclosed in U.S. Pat. No. 5,014,284 by Langer et al., incorporated by reference. A digital radio transmitter is known to one skilled in the art and an example is described in Motorola Application Note AN980 using FSK techniques. If a threshold event is detected, the patient station 14 calls the central station 16 and transmits the electrocardiogram to the central station 16.

The tele-link 102 comprises a radio receiver 126 similar to the aforementioned Ungar patent or if a digital radio receiver 128 is used, similar to the LAWN wireless modem product manufactured by O'Neill Communications, Princeton, N.J. Arrythmia analysis systems are well known and are mentioned in the Ungar U.S. Pat. No. 3,724,455 or U.S. Pat. Nos. 3,536,062 and 4,221,223, both incorporated by reference, which measure heart rate and can provide an alarm if there is high heart rate, and U.S. Pat. Nos. 4,202,340 and 4,184,493 by Langer, incorporated by reference, which can detect Ventricular Fibrillation. U.S. Pat. No. 4,630,204, incorporated by reference, describes an electrocardiogram detection system. Modems 132, 19 are commonly found in today's computers and are manufactured by Hayes and others as well as being described in application notes by VLSI and Silicon Systems, semiconductor chip manufactures. The use of an autodialer to send electrocardiogram data is disclosed in U.S. Pat. No. 4,202,322 by Gessman, incorporated by reference. A DAA 134 (direct access arrangement) is necessary to connect to the phone line.

Figure 3:
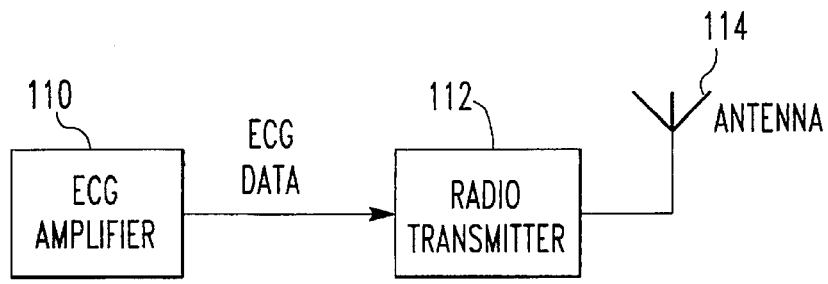
FIG. 3 is a schematic representation of an analog embodiment of a patient transmitter.

More specifically, when the patient transmitter 102 is a fully analog system as shown in FIG. 3, the electrocardiogram amplifier 110 takes the electrocardiogram from the electrodes 32 and amplifies the signal, which it then provides to the radio transmitter 112. The radio transmitter 112 then transmits it by way of antenna 114, to the tele-link 102.

Figure 4:
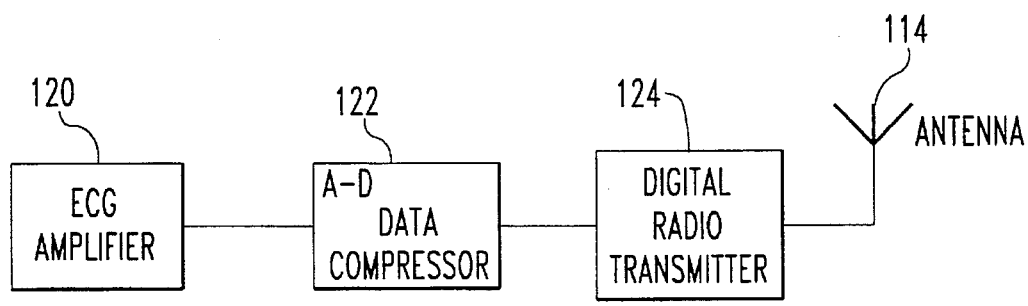
FIG. 4 is a schematic representation of a digital embodiment of a patient transmitter.

If the electrocardiograph signal is transmitted digitally, then the electrocardiogram amplifier 120, as shown in FIG. 4, receives the electrocardiograph signal from electrodes 32, amplifies it and provides it to an analog to digital and data compressor 122 which is essentially a single chip microcomputer. The digitized compressed signal is then provided to a digital radio transmitter 124 which transmits the signal via antenna 114 to antenna 116 of the tele-link 102.

With respect to the tele-link 102 as shown in FIG. 5, the radio receiver 126 receives the transmitted signal from antenna 116 and provides a signal to the first computer 17 which has electrocardiogram analysis. If the signal has been digitized, then the alternate digital approach as shown in FIG. 5 is utilized where a digital radio receiver 128 receives the signal from antenna 116 and provides it to a data decompressor 130 which decompresses the signal so the first computer 17 can analyze the signal. If a predetermined cardiological event is determined to have occurred by the first computer 17, then the electrocardiogram which has already been compressed is provided through a modem with an autodialer 132 through a DAA 134 to the telephone lines 20. The first computer 17 operates the telecommunications linkage.

Audio and visual alarms on the central station 16 are then activated to alert the proper medical personnel at the hospital. The second computer 26 retrieves data on the patient having a threshold event from the database 18 and displays it on the display screen 28 along with the electrocardiogram and its diagnosis by the first computer 17. The patient data contains a medical history, prescribed drugs and instructions on what to do for critical heartbeat irregularities. The second computer 26 also constructs an alarm table which includes past occurrences of diagnosed threshold events and prescribed responses thereto. A doctor then analyzes the data of the central station 16 and comes to a judgment as for what medical action should be taken. If for example, the doctor ascertains that the patient is in danger, he can call the patient directly through the system 10 and/or send for ambulatory transport.

If the patient 11 wishes to manually cause his electrocardiogram to be recorded, as opposed to it only being recorded when a threshold event is identified by the first computer 17, he pushes a button 104 and holds it until a beep is produced by the microprocessor 101. The recorded electrocardiogram can be stored in memory in the first computer 17 to be used when desired. Additionally, the microprocessor 101 is programmed to sound a beep whenever the patient 11 is out of range of the tele-link 102.

A physician of the patient 11 in possession of the secondary station 200 interfaces with the patient station 14 by calling the phone number of the patient station 14 which can be, for instance, a phone number of the patient's residence. The modem 204 of the secondary station communicates with the modem 132 of the patient station 14. Once connected, the patient station 14 is activated to send electrocardiogram information of the patient 11 to the secondary station 200. For instance, the first storage device 208 can be accessed to retrieve the detected cardiological events of interest. The second storage device 210 can also be accessed to retrieve the most recent electrocardiogram of the patient. The electrocardiogram information specified by the secondary station 200 is retrieved by the microcomputer 17 and is transmitted by the modem 132 of the patient station, through the telecommunication line 20 to the modem 204 of the secondary station 200. The electrocardiogram information is then displayed on the terminal of the patient station computer 214 for review by the physician. The electrocardiogram information can also be printed with a printer 216 of the secondary station 200. If the patient station 14 has only one telecommunication line 20, the disconnecting means 212 of the patient station's microcomputer 17 automatically disconnects the secondary station 200 from the patient station 14 if a predetermined cardiological event occurs during the interfacing of the secondary station 200 with the patient station 14 so that the central station 16, which is preferably the hospital, can be notified.

If two telecommunication lines 20 and 21 are provided at the patient station 14, the secondary station 200 can call the patient station 14 through the second telecommunication line 21. When a predetermined cardiological event happens, the physician at the secondary station can remain in continuous contact with the patient station 14 through the second telecommunication line 21 while the patient station automatically notifies the central station 16 of the detected cardiological event.

The system 10 can also be configured such that the secondary station 14 interfaces with the patient station 14 through the central station 16. In this embodiment, the physician in possession of the secondary station 200 calls the appropriate phone number of the central station to connect the modem 204 of the secondary station 200 with the modem 132 of the central station. Central station 16 then calls the patient station 14 for communication therebetween.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A system for monitoring health conditions of a patient comprising:

a patient station having means for generating an electrocardiogram of the patient and a patient transmitter for transmitting information relating to the electrocardiogram, including means for automatically transmitting the information when a predetermined event occurs, said patient transmitter having a first telecommunication line, said patient station has means for disconnecting a secondary station from the patient station when a predetermined cardiological event occurs such that the patient station can transmit electrocardiogram information to the central station over the first telecommunications line;

means for storing electrocardiogram information, said storing means in communication with the generating means, said storing means comprising a first storage device for storing predetermined cardiological events and a second storage device for storing the electrocardiogram generated by the generating means and means for detecting predetermined cardiological events of the patient, said detecting means in communication with the generating means;

a secondary station remote from the patient at the patient station having a modem for creating a communication channel between the patient station and the secondary station such that information relating to the monitored electrocardiogram can be transmitted from the patient station to the secondary station, said secondary station in communication with the patient station, said secondary station in communication with said first telecommunication line said patient station has means for disconnecting the secondary station from the patient station when a predetermined cardiological event occurs such that the patient station can transmit electrocardiogram information to the central station over the first telecommunication line;

a database in communication with the secondary station which provides data about the patient which supplements the information to the secondary station when the information is transmitted from the patient;

a central station in communication with the patient transmitter for automatically receiving the electrocardiogram transmitted by the patient transmitter when a predetermined cardiological event has occurred;

a database in communication with the central station for storing and providing patient data to the central station when a predetermined cardiological event occurs; and display means in communication with the central station and the database for displaying the patient data and the transmitted electrocardiogram.

2. A method of monitoring health conditions of a patient comprising the steps of:

providing the patient with a device for monitoring a predetermined bodily function of the patient at a patient station;

transmitting from a transmitter of the device information about the predetermined bodily function monitored by the device when a predetermined event occurs;

activating the patient station from a secondary station remote from the patient at the patient station by dialing a phone number of the patient station to create a communication channel between the patient station and the secondary station such that information relating to the predetermined bodily function of the patient can be transmitted to the secondary station by the device at the patient station; and providing data about the patient which supplements the information when the information is transmitted.

3. A method as described in claim 2 wherein the providing step includes the step of providing the patient with a device for generating an electrocardiogram of the patient.

4. A method as described in claim 3 wherein after the providing step, there is the step of taking an electrocardiogram of the patient at the patient station.

5. A method as described in claim 4 wherein after the taking an electrocardiogram step, there is the step of storing information relating to the electrocardiogram and the activating step includes the step of retrieving stored electrocardiogram information.

6. A method as described in claim 5 wherein after the taking step, there are the steps of:

automatically detecting predetermined cardiological events in the electrocardiogram;

automatically transmitting the electrocardiogram to a central station remote from the patient at the patient station along with identification of the patient if a predetermined cardiological event has occurred;

automatically retrieving data about the patient having a predetermined cardiological event from a database in communication with the central station; and automatically transmitting the data to the central station from the database.

7. A method as described in claim 6 wherein after the transmitting step, there is the step of displaying the electrocardiogram and the corresponding patient data at the central station.

8. A method as described in claim 7 wherein before the taking step, there is the step of programming the patient station with patient identification and a phone number of the central station.

9. A method as described in claim 8 wherein the automatic detecting step includes the step of notifying the patient at the patient station.

10. A method as described in claim 8 wherein after the retrieving step, there is the step of contacting the patient at the patient station.

11. A system for monitoring health conditions of a patient comprising:

a patient station having means for generating an electrocardiogram of the patient and a patient transmitter for transmitting information relating to the electrocardiogram, including means for automatically transmitting the information when a predetermined event occurs, said patient transmitter includes a first telecommunication line and a second telecommunication line;

means for storing electrocardiogram information, said storing means in communication with the generating means, said storing means comprising a first storage device for storing predetermined cardiological events and a second storage device for storing the electrocardiogram generated by the generating means and means for detecting predetermined cardiological events of the patient, said detecting means in communication with the generating means;

a secondary station remote from the patient at the patient station having a modem for creating a communication channel between the patient station and the secondary station such that information relating to the monitored electrocardiogram can be transmitted from the patient station to the secondary station, said secondary station in communication with the patient station, said secondary station in communication with the first telecommunication line;

a database in communication with the secondary station which provides data about the patient which supplements the information to the secondary station when the information is transmitted from the patient;

a central station in communication with the patient transmitter for automatically receiving the electrocardiogram transmitted by the patient transmitter when a predetermined cardiological event has occurred, said central station in communication with the second telecommunication line;

a database in communication with the central station for storing and providing patient data to the central station when a predetermined cardiological event occurs; and display means in communication with the central station and the database for displaying the patient data and the transmitted electrocardiogram.

12. A system for monitoring health conditions of a patient comprising:

a patient station having means for generating an electrocardiogram of the patient and a patient transmitter for transmitting information relating to the electrocardiogram, including means for automatically transmitting the information when a predetermined event occurs;

means for storing electrocardiogram information, said storing means in communication with the generating means, said storing means comprising a first storage device for storing predetermined cardiological events and a second storage device for storing the electrocardiogram generated by the generating means and means for detecting predetermined cardiological events of the patient, said detecting means in communication with the generating means;

a secondary station remote from the patient at the patient station having a modem for creating a communication channel between the patient station and the secondary station such that information relating to the monitored electrocardiogram can be transmitted from the patient station to the secondary station, said secondary station in communication with the patient station;

a database in communication with the secondary station which provides data about the patient which supplements the information to the secondary station when the information is transmitted from the patient;

a central station in communication with the patient transmitter for automatically receiving the electrocardiogram transmitted by the patient transmitter when a predetermined cardiological event has occurred, said secondary station communicates with the transmitter of the patient station through the central station;

a database in communication with the central station for storing and providing patient data to the central station when a predetermined cardiological event occurs; and display means in communication with the central station and the database for displaying the patient data and the transmitted electrocardiogram.

13. A system as described in claim 12 wherein the central station includes a central transmitter for transmitting information to the patient station and the patient station includes a remote receiver for receiving information from the central station.

14. A system as described in claim 13 wherein the detecting means of the patient station includes a first computer having a program which analyzes the electrocardiogram and causes the electrocardiogram to be transmitted to the central station when a predetermined cardiological event occurs.

15. A system as described in claim 14 wherein the central station includes a second computer, and the display means includes a display screen electrically connected to the second computer.

\* \* \* \* \*